United States Patent
Daneshvar

[11] Patent Number: 5,419,757
[45] Date of Patent: May 30, 1995

[54] SUPPORT CONTAINING SHAPED BALLOONS

[76] Inventor: Yousef Daneshvar, 21459 Woodfarm, Northville, Mich. 48167

[21] Appl. No.: 997,526

[22] Filed: Dec. 28, 1992

[51] Int. Cl.6 .................................................. A61F 13/00
[52] U.S. Cl. ........................................ 602/60; 602/61; 602/62; 602/63; 602/74; 604/304; 128/DIG. 20; 606/204.15
[58] Field of Search ............... 128/DIG. 20; 602/13, 602/48, 53, 60, 61, 62, 63, 64, 65, 74; 604/304, 307, 308; 606/201, 202, 203, 204, 204.15

[56] References Cited

U.S. PATENT DOCUMENTS

| | | | |
|---|---|---|---|
| 3,993,056 | 11/1976 | Rabischong et al. | 602/13 |
| 4,084,586 | 4/1978 | Hettick | 602/60 |
| 4,224,945 | 9/1980 | Cohen | 602/53 |
| 4,378,009 | 3/1983 | Rowley et al. | 602/13 |
| 4,399,816 | 8/1983 | Spangler | 128/888 |
| 4,628,918 | 12/1986 | Johnson, Jr. | 602/13 |
| 4,657,003 | 4/1987 | Wirtz | 602/13 |
| 4,682,587 | 7/1987 | Curlee | 602/13 |
| 4,682,588 | 7/1987 | Curlee | 128/DIG. 20 |
| 4,706,658 | 11/1987 | Cronin | 602/13 |
| 4,730,610 | 3/1988 | Graebe | 120/DIG. 20 |
| 5,031,609 | 7/1991 | Fye | 602/74 |
| 5,171,211 | 12/1992 | Deasy, Jr. | 602/60 |
| 5,230,695 | 7/1993 | Silver et al. | 602/134 |

Primary Examiner—Paul Prebilic

[57] ABSTRACT

Various support devices have one or more balloons that are strapped around a portion of the body with a soft layer between them and the body. In some devices, the balloons are separably mounted a strap that encircles a portion of the body. Various forms of balloons are disclosed. In other devices, the balloon has an open area that is disposed over a bony prominence or ulcerated area. An insert for applying medicine may be disposed within the open area. Certain devices are for body joints and therefore have multiple parts that can move toward and away from each other as the joint flexes.

10 Claims, 13 Drawing Sheets

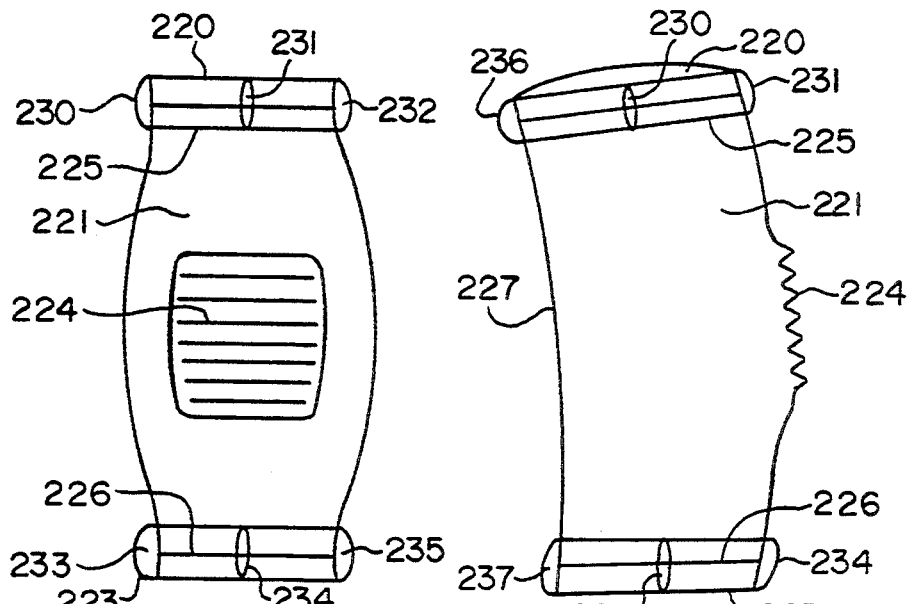
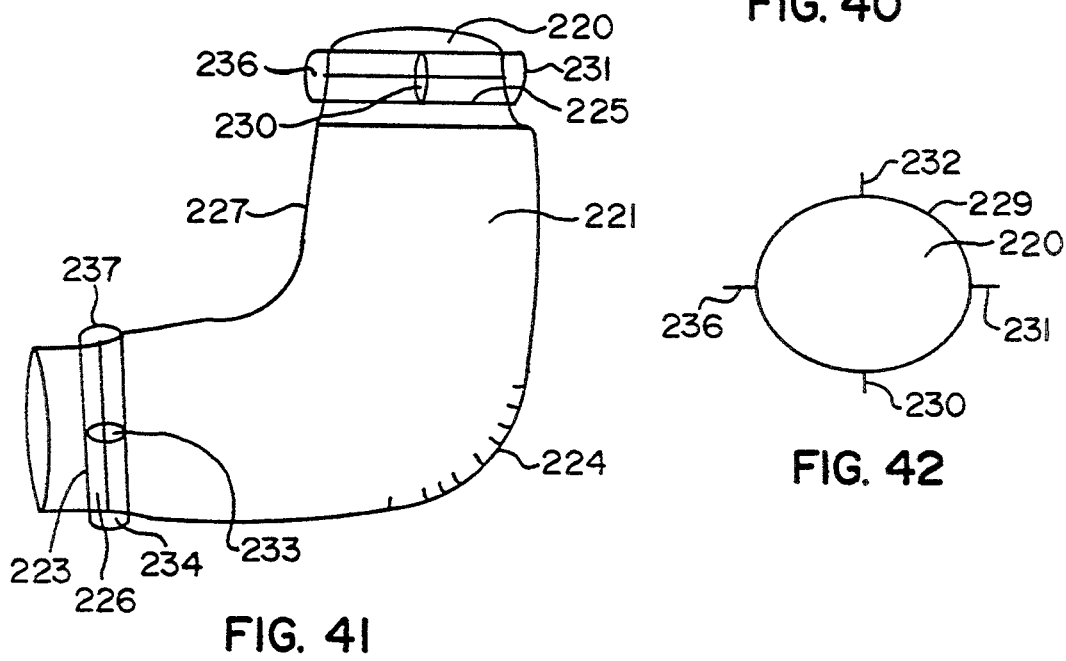

SUPPORT CONTAINING SHAPED BALLOONS

BACKGROUND OF THE INVENTION

Certain diseases and conditions, such as old age, chronic or major diseases, accidents, surgeries, etc., often cause a serious mobility problem for a person. They can bring about their own major complications, such as ulcerations and bedsores, etc., especially when a person cannot move and stays in the bed, mostly in one position. In these circumstances, the pressure on the skin area, constantly pressed by the adjacent bones (mostly joints) from one side and by the surface of the mattress from the other, will cause gradual deterioration of the nutrition of the skin and underlying tissues, and ultimately ulcerations in that spot. Unfortunately, they are usually bad and very hard to treat, when the cause cannot be cured or eliminated. Ulceration does occur in any place where the skin is pressed against a hard surface, but is specially common in the lower back over the spine, in the ankles, in the heels, and sometimes in the knee area and side of the legs, back of the head, and again in any spots of skin over the bone that for one reason or another are pressed against a surface for a long time. The treatment is not easy as long as the cause cannot be eliminated and the pressure to the area continues to occur.

Observation of such patients during my career as a doctor made me think and finally offer a technique for supporting these areas and sores as well as for preventing damage to the areas. To my knowledge, this is new and genuine, and I believe it will work most of the time if used properly. It will also allow local treatment to be provided without a need for opening the whole unit. The technique, with some modification, can also be very helpful after many surgeries, as well as supporting the neck of a patient.

BRIEF EXPLANATION OF THE INVENTION

This invention is primarily related to making units from a piece of balloon that can be permanently or temporarily inflated to maintain air inside it. This balloon has a rather flat surface covered by a layer or layers of soft material, such as soft, non-irritant, thick fabric with fluffy surface, or a lambskin and/or soft plastic bubbles. This unit is made either from one balloon or preferably combinations of multiple balloons that absorb pressure and stay in place appropriately. The main balloon may be divided by walls to make compartment of balloons that will serve this purpose. This basic unit is shaped in different ways to construct other units that are used for protection of the back, ankles, elbows, neck, etc. In these cases, the units are shaped to go around the place desired to be used and joint(s) and the area which are intended to be protected. However, when the skin has ulceration in the area, then the unit has an opening or hole or empty protected space in the area over the ulceration so that the pressure on the ulcer spot is prevented. This unit is kept in place with the use of Velcro TM patches. Very importantly, the opening in the unit allows the skin care to be given when necessary, without a need to remove the whole unit. For example, the unit for the back allows the patient's skin to be cleaned and dressed with medications. Another unit goes around the neck and is held in proper position as required. Units that support and help in shaping operated sites are also mentioned in this application.

BRIEF DESCRIPTION OF THE DRAWINGS

FIGS. 39 and 40 are rear and side views of a sixteenth embodiment.
FIG. 41 is a view similar to FIG. 40 showing a different position for this embodiment.
FIG. 42 is an end view of the sixteenth embodiment.

DETAILED DESCRIPTION OF THE INVENTION

Figure 1:
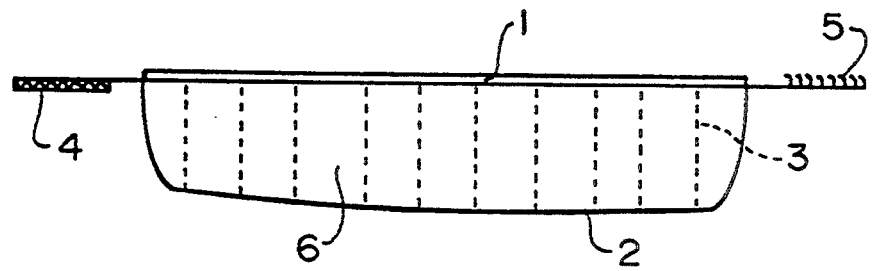
FIG. 1 is a top view of a first embodiment.

The invention generally involves specially shaped balloons to protect the areas and spots that are under pressure. A unit is made from balloons that can be permanently or temporarily inflated to maintain air or fluids inside. The fluid may be chosen with different consistency and different temperature. (When the fluid is used, an opening for air escape is added to the balloon.) This balloon has a rather flat surface on one side covered by a layer, or layers of soft material, such as soft, non-irritant, thick fabric with fluffy surface, or a lambskin and/or layer of soft plastic with a layer of soft bubbles under the soft cover. The main body of this unit is made either from one balloon, or preferably combinations of multiple balloons, that absorb the pressure, and have a shape and are supported to stay in the intended places appropriately. The main balloon can be divided by walls to make compartments of smaller balloons that will serve this purpose. A balloon which is divided into smaller balloons or is made from combinations of balloons may then have different ports of inflation to allow different groups of the balloons to be inflated either at different times or with different pressures or to give the important chance of inflating them periodically or alternatively.

The soft material covering the inner surface of this unit gives the skin a chance to enjoy a soft, cozy, and non-irritating surface of the unit while the outer surface, the thickness and shape of the unit prevent the surface of the mattress from touching it. I would like to indicate that unfortunately most mattresses, even some of the soft-covered beds, have not been an answer to this problem of bedsores, since they do not prevent the prominent parts of the body from touching the surface of the bed and standing on it for a long time, which is the unfavorable condition that occurs when the area is sore. The use of sponges has not been the answer either, since they are compressed and act like rough units themselves. My basic unit explained above is shaped to match the different anatomy of the areas with which it is intended to be used.

A matrix of plastic made from combinations of hard and soft plastic allows the shaping of my unit to be obtained and pieces of harder plastic help to avoid pressure of the balloons at certain important areas. It is intended to use this matrix to make a skeleton that may be needed in giving shape to the unit and having the shape of the balloons under control. Some pieces of this matrix may be like a thread going over the balloons to control their shape.

A plastic cover will be useful to protect the ulcer spots from pressure too. Since after the ulcer is healed, or in cases where the ulcer has not yet developed, a complete opening over the spot may not be truly necessary, and at this stage, if the prominent spot was only protected from the pressure, it should be sufficient. Therefore, for such uses, units are chosen that although the opening is not present, have a protective plastic piece that is used to prevent the unit from pressing on the point of sore or tender spot. Again, a screen of softer, non-stretchable plastics, or units like screens with desired shapes, is quite helpful in giving the shape to this unit.

These units are also very useful for treatment of injuries to the joints. In these cases, a unit can be chosen to immobilize the joint for the period for which it is required. For this purpose, the shapes that are made from one solid balloon combination will be more useful. Also, these are the cases for which use of fluid for filling the balloons will be more desirable, since it will give the chance of choosing the temperature, which can be very beneficial. For example, in early trauma where immobilization and the use of ice are recommended, the balloon may be filled with ice water to keep the area cold, and later, when heat is recommended to diminish the pain, warm water can be infused into the balloon. Also, if higher pressure were to be used to prevent spread of hematoma and swelling, then the pressure inside the balloon can be increased. These are all new possibilities with the use of one unit.

Alternatively, a support unit can be made from a soft but non-stretchable fabric that has a surface covered with patches of Velcro TM. This unit allows sticking different sizes of balloons having a surface covered with matching patches of Velcro TM. A combination will allow the balloons to be changed, and different balloons to be used when a balloon is popped or ruptured.

In order to further secure the shape and effectiveness of the unit, a cover of latex may be used and rolled or pulled to go over all of the unit in place. When functional, then the elasticity of this piece with its internal capacity of adapting the shapes will be very beneficial in helping to reach its overall purpose so that it will hold the whole unit in place and protect it. This elastic cover also gives the advantage that prevents dirt from going into the unit. An exchange is easily possible if needed. A model of this unit may also have a soft fortified rim in its ends so that it prevents water from reaching inside the unit, and this allows the areas above and below the unit to be washed without disturbing the covered area. The rim may be further fortified by having three parallel lines of round fortified latex lines to function like three parallel collars around the limb, and this will most probably prevent water from entering under the unit most of the time. The areas on the tip of joints are designed to have extra wall, like a wall of an accordion, that allows the wall to be functional when the joint is bent. This is very advantageous to prevent disfigurement of the unit when it is bent. This cover would make a distinct advantage in many cases. At the time of use, this cover can be pulled or rolled over the unit.

Figure 2:
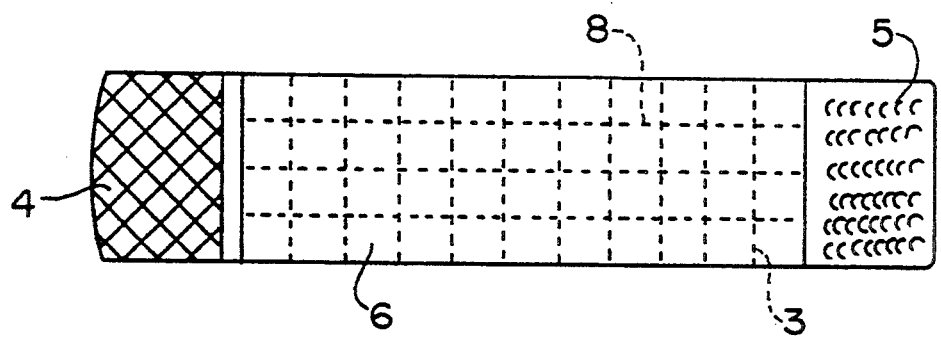
FIG. 2 is a front view of FIG. 1.
Figure 3:
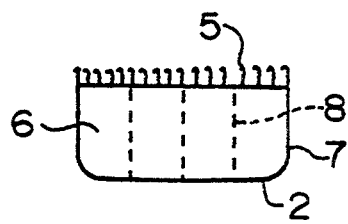
FIG. 3 is a right end view of FIG. 2.

FIGS. 1–3 show a general embodiment of the invention. The base of the unit is a soft cover 1. The surface of the balloon is 2, the short inner walls of the balloon are 3, one small compartment of the balloon is 6, a soft Velcro TM piece 4 is at one end and a rough Velcro TM piece 5 is at the other end. The long walls are shown by dotted lines 8. One side of the balloon is 7.

Figure 4:
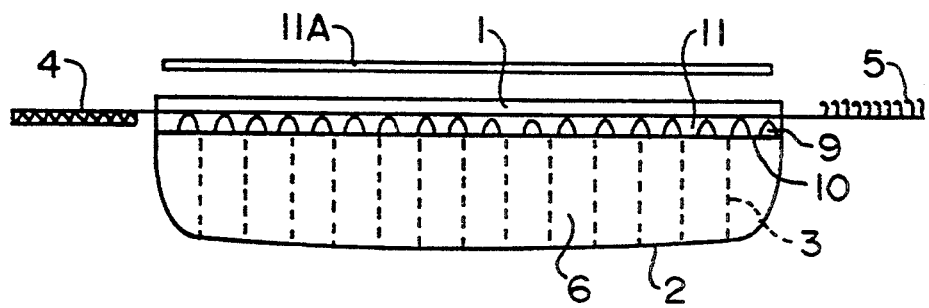
FIG. 4 is a top view of a second embodiment.

FIG. 4 is very similar to FIG. 1, except this unit has a layer of soft plastic bubbles 9, which is on the base 10 of the big balloon. The spaces between the smaller bubbles, or balloons, are 11. FIG. 4 also shows an optional disposable inner liner 11A for placement in underlying relation to cover 1 so as to be between the person and cover 1 when the support is applied to the person.

Figure 5:
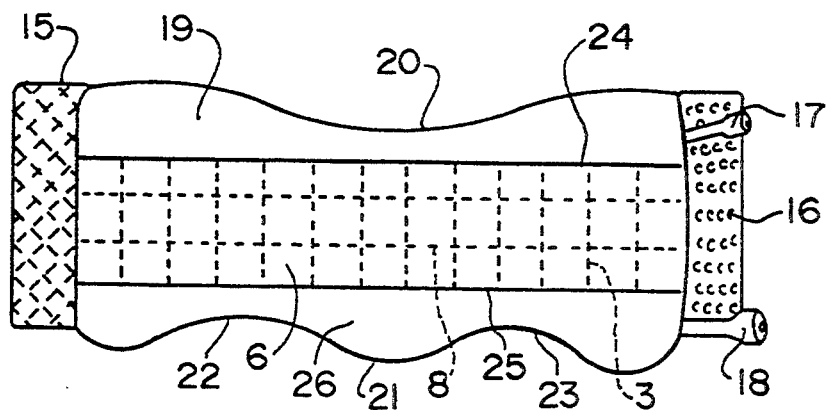
FIG. 5 is a front view of a third embodiment.
Figure 8:
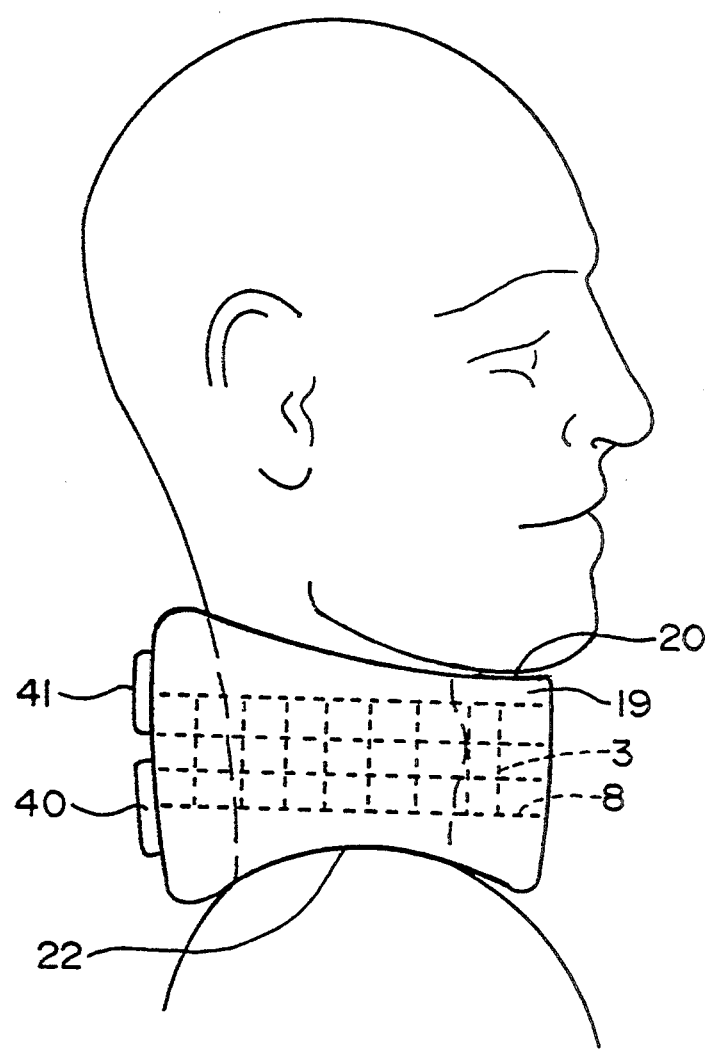
FIG. 8 is a side view of the FIG. 7 embodiment in use.

FIG. 5 shows a unit that is made from a unit very similar to the one shown in FIG. 1, except this unit has an upper and a lower layer of soft balloon that are specially shaped so that this unit can work as a cervical collar as shown in FIG. 8. The center balloon is shown with its upper wall 24 and its lower wall 25, and it is divided by the long horizontal walls 8 and the shorter vertical walls 3 into compartments 6. The upper horizontal balloon 19 has a valley 20 in its upper rim for the lower chin/upper neck area. The lower horizontal balloon has valleys 22 and 23 to allow it to stand on top of the upper shoulders and a rise 21 that is to stand in the front of the lower neck/upper chest area. The upper balloon has an inflation port 17, and the lower balloon, an inflation port 18. One end has a soft Velcro TM piece 15 and the other end, a rough Velcro TM piece 16.

Figure 6:
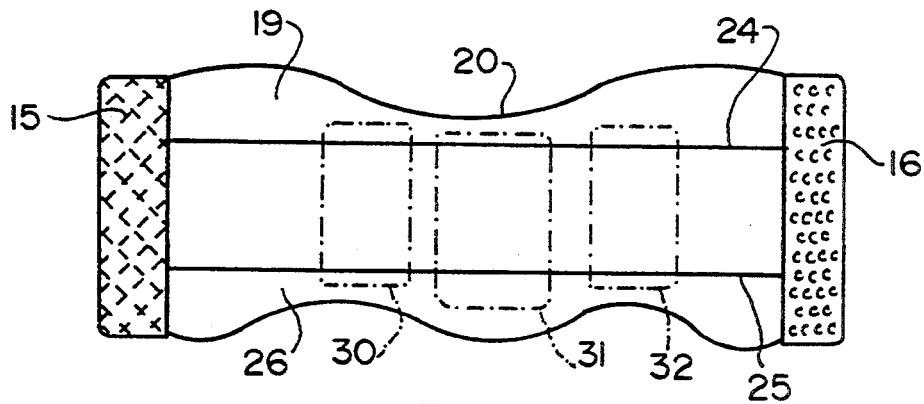
FIG. 6 is a front view of a fourth embodiment.

FIG. 6 is similar to the unit shown in FIG. 5, except this unit has protective pieces 30, 31, 32 of plastic in its wall to protect the sensitive areas of the neck from excessive pressure by balloons. The borders of these plastic walls are shown by dash and dot lines.

Figure 7:
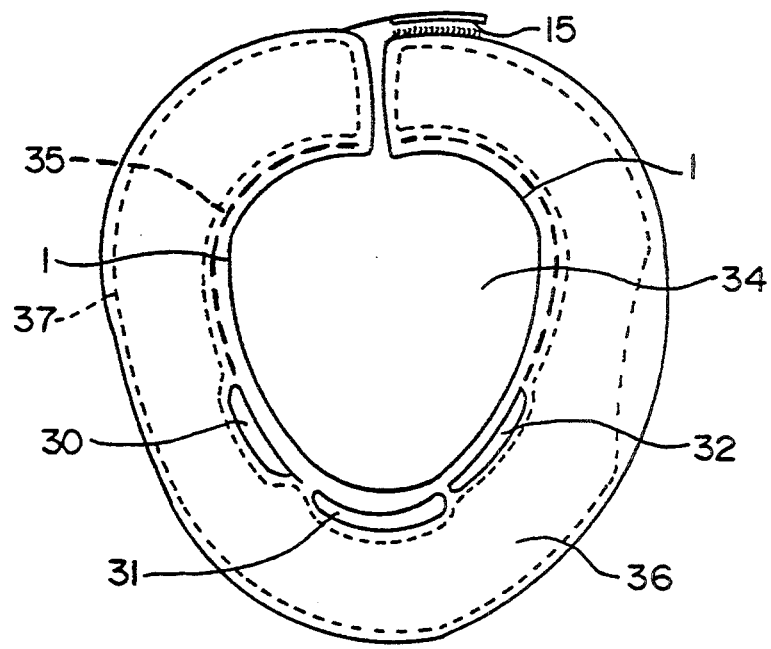
FIG. 7 is a top view illustrating a use position of FIG. 6.

FIG. 7 is a view of a unit similar to the one shown in FIG. 6 that is curled to go around the neck of a person. The inner space where the neck will be placed is shown at 34, and the inner surface is shown at 1. A protective screen of plastic is shown by a heavy broken line 35 and has protective pieces of plastic 30, 31, 32 in its front area. Borders of the balloon are shown by dotted line 37, and the balloon's inner lumen by 36. The ends of this unit come together and are connected to each other by straps, one end of one of which is shown in the upper side of this Fig. at 15.

FIG. 8 shows a person using a unit similar to the one shown in FIG. 6. This figure shows the upper border to this unit, including valley 20, and the upper horizontal balloon 19. The middle large balloon divided by horizontal lines 8 and vertical lines 3 is shown in the center. The valley 22 is also shown, and the rear ends of this unit are held together by straps 40 and 41.

The cervical collar is made from a body of the balloons similar to one mentioned earlier that has been divided by internal walls to many compartments. This unit is covered by a soft comfortable lining as mentioned. This unit has a size and shape to wrap around and stand around the neck and to hold the neck in proper position. This unit is to be held in place by having the ends of the unit stick to each other and held in place with use of Velcro TM patches, or straps that will go from one side to stick to the other. The center piece has upper and lower balloons with the special shape shown in FIG. 5 and 6. This units to have their own independent inflation ports and are individually inflatable so that their size and relative shape can be changed and adjusted easily to match the shape of the neck of the user. These pieces have their own inflation port with related valves. These valves may have an automatic closure system so that they will close after the inflation bulb or the syringe is removed. The advantage of this unit is that in contrast to the readily available units, it will be lighter and importantly its shape is adjustable and the pressure inside can be controlled. The upper and lower balloons will make it possible for the unit to match the shape of the upper chest and the lower chin area of the person using it so that it would be more comfortable. This would be possible due to the fact that the balloon's shape will adjust and it will reshape and remodel to some degree, to give more room for the more pressured area and to fill the areas that have lesser pressure. While the body of the unit will maintain the desired shape for the whole unit. It will be possible to make the construction of the middle part more stiffer if it is desired. Alternatively, a colorful stiffer piece may be added to go around the middle balloons to make it more stiffer too. The inner part of the unit may have a piece of stiff plastic embedded under its lining in front of the great vessels of the neck and the trachea to prevent from the pressure to these sensitive parts. Also, a network or skeleton of plastic can be used to give shape and protection and body to the units when and as much as required. Pieces of synthetic foams may also be used in construction of this unit. This unit is to be used to support the neck of a patient and keep it in a medically desired position.

Figure 9:
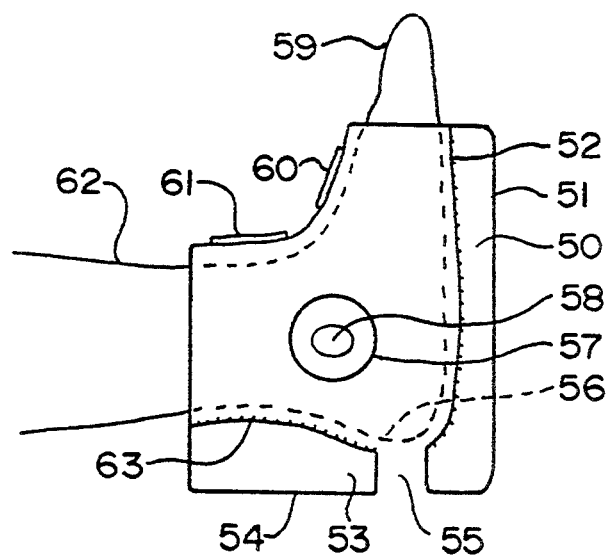
FIGS. 9, 10, and 11 are right side, top, and left side views of a fifth embodiment in use.
Figure 10:
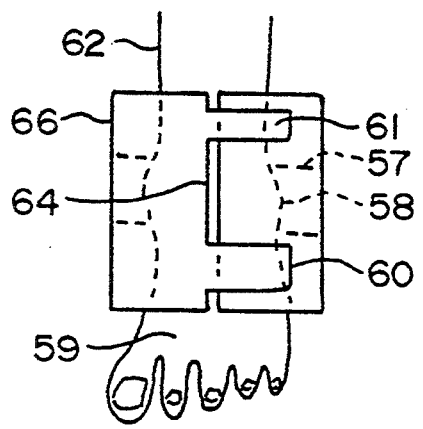
Figure 11:
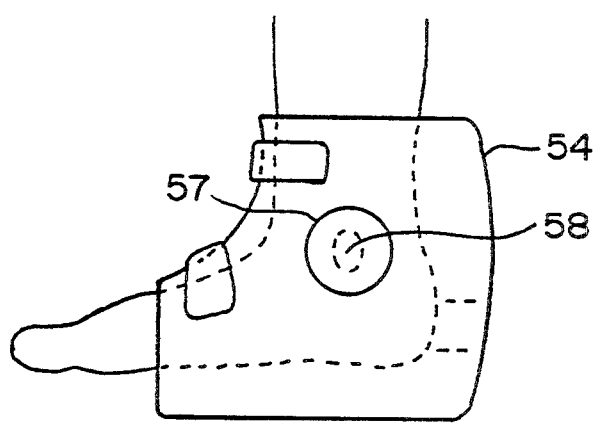

FIGS. 9-11 show a person's ankle that is wearing an ankle support made from a unit similar to the unit shown in FIG. 1. This unit has a matching shape that goes around the ankle and has one end sticking to the other in front with the use of Velcro TM patches. This unit has openings in front of the prominent points of the heel and the inner and outer sides of the ankle joints. The lower leg is 62, and the upper surface of the tip of the foot is 59. The lower piece of this unit, which is a balloon standing and covering the sole of the foot, is shown at 50. The outer surface of this piece is shown at 51, and the inner surface of this unit which has a soft cover is shown at 52. The upper rear side of this unit is shown at 53, and it has an outer surface shown at 54 and an inner surface shown at 63. The hole in front of the rear prominent point of heel 56 is shown at 55, and the opening of the wall in front of the prominent point of the outer ankle 58 is shown at 57. The front of this unit is in front of the foot and its edges are held together by the short straps 60 and 61 containing the Velcro TM patches. The outer surface of the inner side of the unit is shown at 66, and the opening in front of the prominent point 67 of the inner surface of the ankle is shown by broken line 65.

The unit for the ankle is made to have a shape to go around the ankle joint and to cover its rear surface and sides by an inflated balloon and to come and join together in the front by a fabric (which may have some elastic component in its construction to hold the unit together) with use of short straps or bands with pieces of Velcro TM patches on the surface of their ends. These openings 55, 57, 65 will give the unique chance that the sore and ulcer spots can be cleaned and dressed and medicated and even exposed to air and heat if desired without a need for removing the whole unit.

A matching patch of the soft balloon will be used to deliver medications. This patch of balloon will have a soft surface which may be covered with layers of gauze and medications that can be placed on the sore spot to provide the treatment. The thickness of this balloon can be chosen and will vary. This smaller balloon patch can be held in place by being taped on the surface of the unit. Alternatively, the main unit may have a strap that will go over and across the opening of the unit to be stuck to the other side of the unit. The tip of this strap will be held in place by having its end to stick to the side of the unit by a Velcro TM patch. When there are sores in the inner or outer prominent areas of the ankle, then a unit may be used with open spaces in front of those sore spots, again to allow the same advantages to be taken, with use of heating lamp cleaning, medicating, etc. Units will be made for the left and right ankles, having shapes where the unit to be used in left ankle is the mirror image of the unit for the right ankle. A universal unit may be made that can be used in each side. A disposable lining may be used under this unit which is explained more later in this application. Among lots of advantages this unit has, it may also prove to save a lot of time when it is used instead of bandaging the ankle in traumas, since it can be easily placed and stuck rather than having a need for skill and time of medical personnel to apply the wrap in the area.

Figure 12:
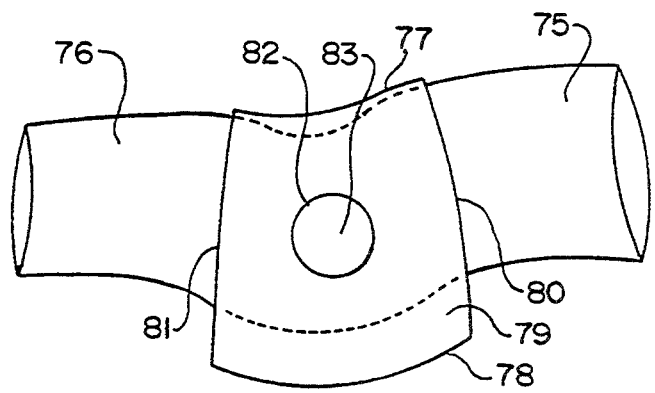
FIGS. 12, 13, and 14 are left side, rear, and front views of a sixth embodiment in use.
Figure 13:
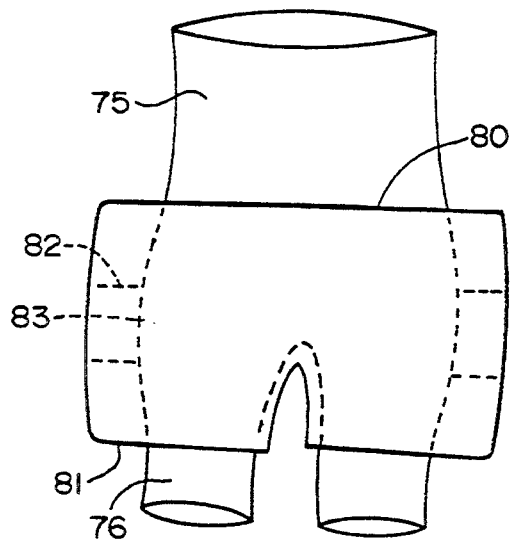
Figure 14:
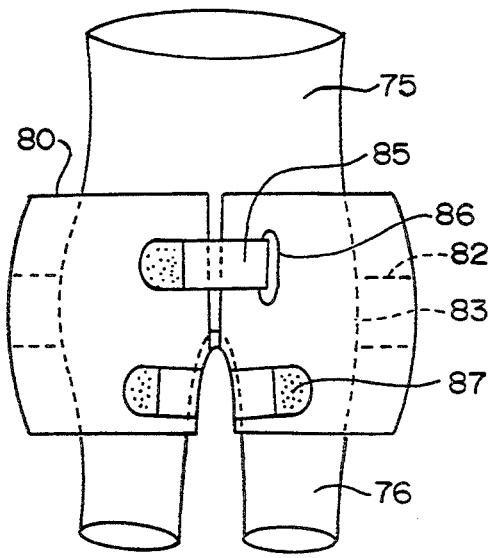

FIGS. 12-14 show a person wearing a hip support made from a unit similar to the unit shown in FIG. 1. This unit has a matching shape that goes around the hip and buttocks and has one end sticking to the other in the front with the use of Velcro TM patches. This unit has openings in front of the prominent points of the hip joint. The trunk of the body is shown by 75 and the left thigh by 76. The balloon that is standing and protecting the buttock is shown by 79 and its outer surface by 78. The front of this unit is shown by 77, its upper rim by 80, and its lower rim by 81. The wall of the opening in front of the prominent part of the hip joint 83 is 82. The ends of this unit come and are held together at the lower part of the abdomen by a strap 85 that goes through a snap 86 to make a U-turn and come and stick to its own matching surface. The lower parts of this unit are held in place around the upper thigh areas by ends of the unit which come and are held tight with a matching part by a strap similar to the one mentioned above. This strap in left side is shown by no. 87.

Figure 15:
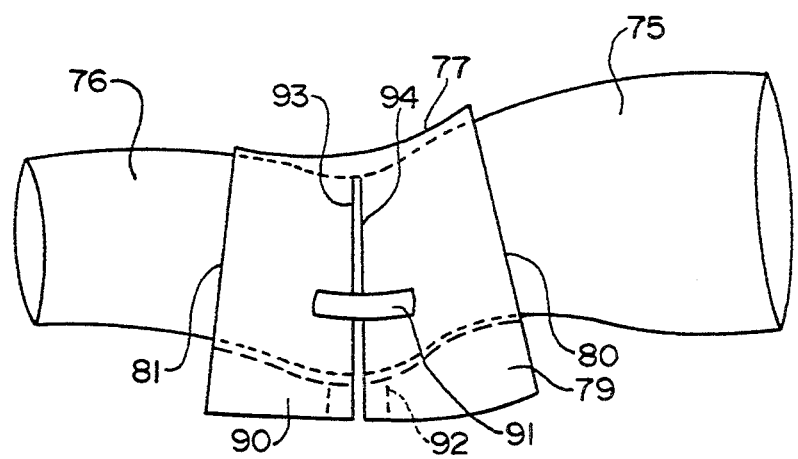
FIGS. 15, 16, and 17 are left side, rear, and front views of a seventh embodiment in use.
Figure 16:
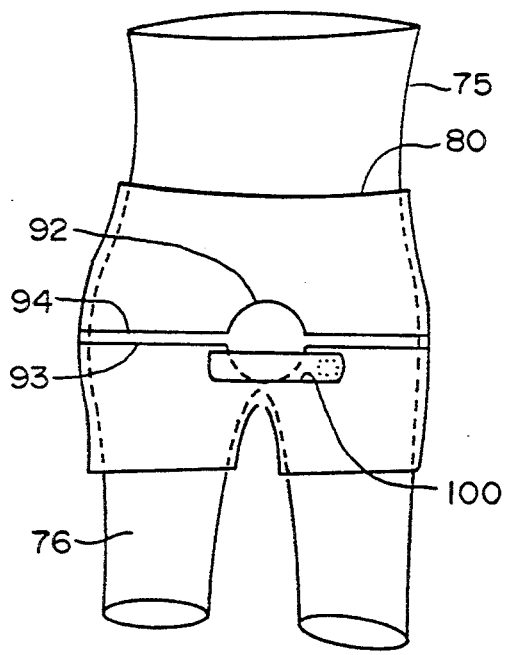
Figure 17:
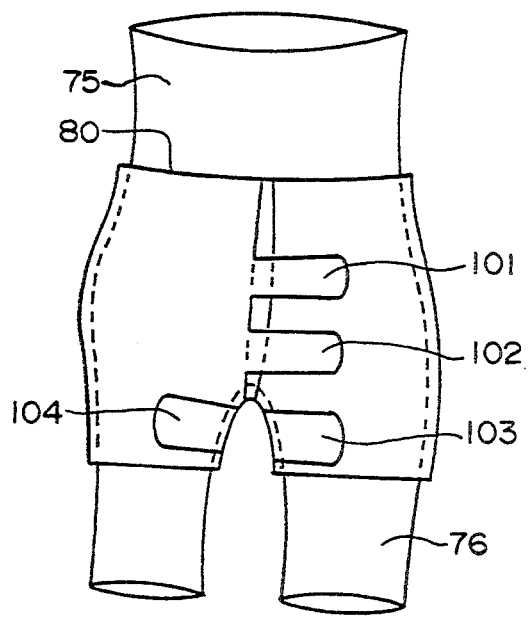

FIGS. 15–17 show a person wearing a hip support unit which is similar to unit shown in FIG. 12, except this unit is made from two pieces, upper and lower, that are held together in front by a common front unit and also by strap 91 in the side that has an elastic component in it. The trunk of the body is 75, and the left thigh 76. The balloon that is standing and protecting the buttock is 79, and the wall of the opening in front of the prominent point of the buttock is shown at 92. The balloon that is standing and protecting the upper thigh and lower buttock is shown at 90. The upper rim of the upper unit is 80 and lower rim of this unit is 94. The upper rim of the lower unit is shown at 93 and lower rim of this unit at 81. The left and right side pieces of the lower unit are held together by a strap 100. The ends of this unit come and are held together in lower side of the abdomen by straps 101 and 102, and the lower parts of this unit are held in place around the upper thigh areas by the ends of the unit coming and being held tight with the matching part by a strap similar to the one mentioned above. These straps are shown at 103 and 104.

The hip support is similar to the other units mentioned earlier. This unit also will be made from combinations of the balloons having a soft cover on the inside surface to prevent discomfort, irritation and inflammation of the skin. The body of the balloons prevents pressure from being applied to the prominent areas or the sore or ulcerated spots. A skeleton or combinations of pieces of soft and hard plastics may be used in make up and the shaping of this unit.

Again, in order to allow the hip joint to bend, this unit will be made from combination of an upper piece and a lower pieces of balloons, which are separated along a horizontal line in the back and in the sides, and the end pieces of these units come to join in front by a common soft and strong pieces of fabric that may have an elastic component in it to be held together by straps to stay in place securely. In the lateral sides, one or more pieces of elastic bands will connect to the upper and lower pieces to help to hold these pieces together securely. This separated construction will allow the hip joints to bend and be functional. The upper piece of this unit has balloons in the back as well as the right and the left side to stand over the buttocks and sides of the hips. The center area of this upper piece has an opening in the back to allow separation of the right and left side pieces for easier mobility of the patient. The lower piece of this unit comprises balloon units that stand around the upper thigh area and its rear and lateral sides but have a fabric piece in the front and inner surface. The front parts of the upper and lower pieces are connected to each other as mentioned above by a natural or synthetic fabrics or straps or wraps which may have elastic components in them. The front piece is to pull the sides and give shape to the unit and allow it to stand in the area as desired. The ends of these units come and are connected to each other by use of straps and snaps and Velcro ™ patches. This construction is to give the mobility required for easy mobilization the patient needs. The thickness of this unit and combinations of the balloons will also allow the unit to absorb the pressure and to protect the hip (to some degree) when the person falls down. The fact that the balloons are pressurized will allow dissipation and absorption of some of the pressure from the fall and to prevent the hip injury or to diminish its impact. Pieces of foam, such as used in foam cups, may also be used to help in this purpose. And a layer of latex may also be used in construction of this unit to help in better functioning of the unit in the same way mentioned for previous units. This unit can be worn by some people in order to protect their hip joint and the buttock area from the full impact of a fall.

Such a unit with some modifications may also be used by some concerned persons who may wish to wear it when they go for a walk when there is some chance of falling or for the older vulnerable persons to use in their home when they are subject to fall and injury. The degree of the protection will depend on the size and construction of the balloons and their material so it will be possible to make more protective units that may get heavier and bulkier.

Figure 18:
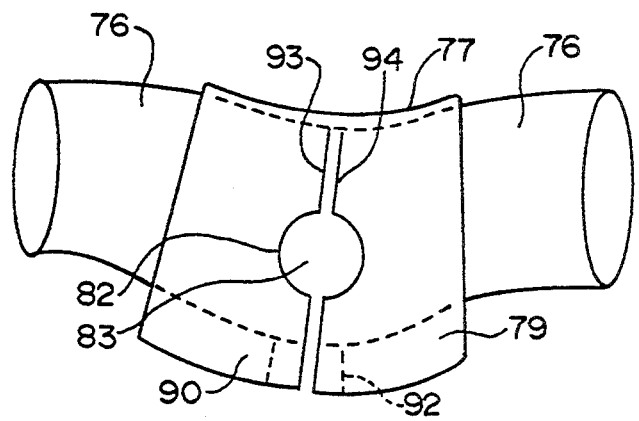
FIGS. 18, 19, and 20 are left side, rear, and front views of an eighth embodiment in use.
Figure 19:
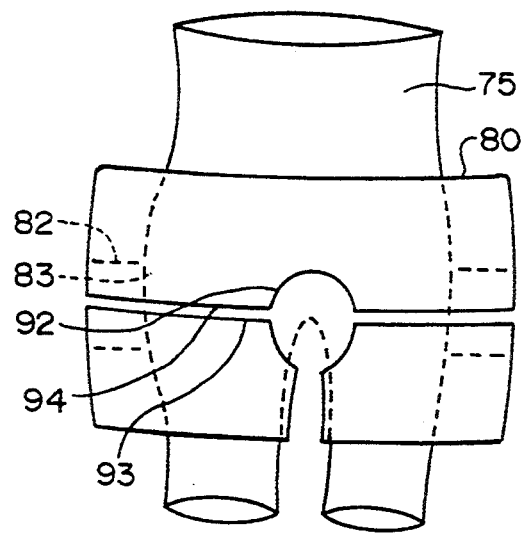
Figure 20:
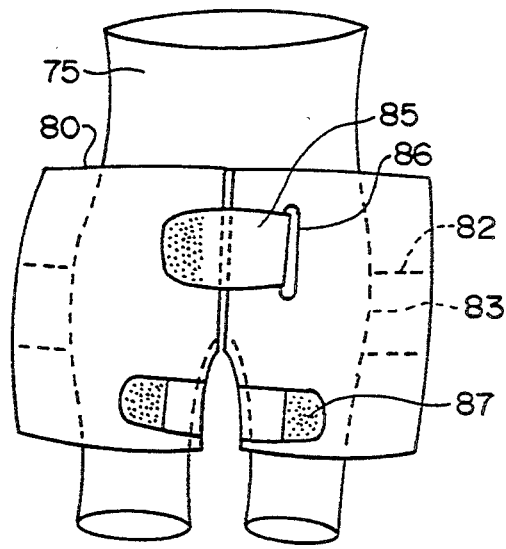

FIGS. 18–20 show a person wearing a hip support unit which is similar to the unit shown in FIG. 15, except this unit also has an opening in front of the prominent point of the side of the hip. This opening will prevent pressure to that spot and protect an ulcer when present. The fact that this unit is made from two separate upper and lower pieces held together gives the advantage that the person can bend his or her hip joint. This unit has also a common front piece, with an elastic component to pull the ends and hold them together. The trunk of the body is shown at 75 and the left thigh 76. The balloon that is standing and protecting the buttock is 79, and the wall of the opening in front of the prominent point of the buttock is 92. The balloon that is standing and protecting the upper thigh and lower buttock is 90. The prominent area of the side of the hip is 83, and its wall is 82. The lower rim of the upper unit is 94, and the upper rim of the lower unit is 93. The common front piece is 77. The upper rim of the upper unit is shown at 80. The ends of this unit come and join and are held together at the lower side of the abdomen by a strap 85 that goes through a snap 86 to make a U-turn and to come and stick to the rear side of its own unit. The lower parts of this unit are held in place around the upper thigh areas by the ends of the unit being held reasonably tight with use of matching straps shown in left side by 87.

The unit for the hip sore provides protection and allow certain care to be provided for patients with ulcerations in their lower back or sides of the hip area due to constant pressure from the bed (bedsores). The general structure and shape of this unit is very similar to the unit mentioned for the hip support. Again, this unit also will be made from combinations of the balloons with a soft cover on their inside surface to prevent discomfort, irritation and inflammation of the skin. Pieces of foam may also be used in construction of this unit. However, in order to allow patient to be able to bend his or her hip joint, this unit may consist from two pieces connected to each other—one upper and one lower. The upper piece of this unit will be similar to one mentioned above except this unit will have openings in the sides, in front of the prominence of the joints in the right and left side, which is to stand on the sides of the hips. The center rear area of this upper piece will have an opening in front of the prominence of the sacrum and prominent points of the spine to allow the ulceration on that area to be exposed to air but not to the pressure. In other words, the opening area will be surrounded by balloons that are higher than the skin and therefore will prevent the ulcer area from touching the surface of the bed. This opening will also allow the local medical therapy to be provided to the area of the ulcer through the opening.

The walls of these openings may be fortified by use of pieces of plastics to prevent their collapse under pressure.

The separated construction of the units will allow separation of the right and left side pieces for easy mobility of the patient. The lower piece of this unit will be very similar to the lower piece previously mentioned unit for hip support, which is pieces of balloons that cover the back and sides of the upper thigh area, and the inner ends of those as well as the front side are made from synthetic fabric, straps or wraps. The front part of these pieces are connected to each other by fabric, straps, or a similar material which may have an elastic component in it. The front piece has again the job of pulling the sides to hold the unit together and to give a shape to the unit and allow it to stand in the area as desired. The ends of these units comes and stick to each other by straps and snaps and Velcro ™ patches. This construction is to give the mobility required for easy mobilization the patient needs. The thickness of this unit and combinations of the balloons will keep the sore spot above the mattress surface. The walls of these openings may be fortified by use of pieces of plastic to prevent their collapse under the pressure. (Pieces of synthetic foam may also be used in construction of this unit.) While the opening will allow the medical care to be provided to the patient. This opening will also make it possible for a matching piece of soft balloons covered with a piece of gauze to be inserted into the open space and be held by tapes connected to the sides of the unit or by a short strap that goes on this opening. This gauze can be medicated to allow application of antibiotics and different medications to the sore (ulcer area). This will give an unusually unique and great chance for the wound to improve when the medicine can be applied and other skin care to be provided when the pressure is being avoided. Exposure to air and use of heat lamps will also be possible through this opening.

This unit will give the chance that when the patient is lying on his back, the prominent area of the back does not touch the mattress, and also when he sleeps on the sides, the prominent points of his sides would not touch the mattress very much either.

Figure 21:
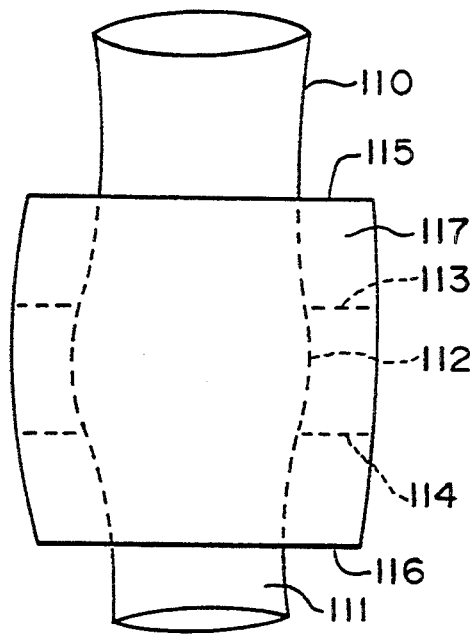
FIGS. 21, 22, and 23 are front, left side, rear, and rear views of a ninth embodiment in use.
Figure 22:
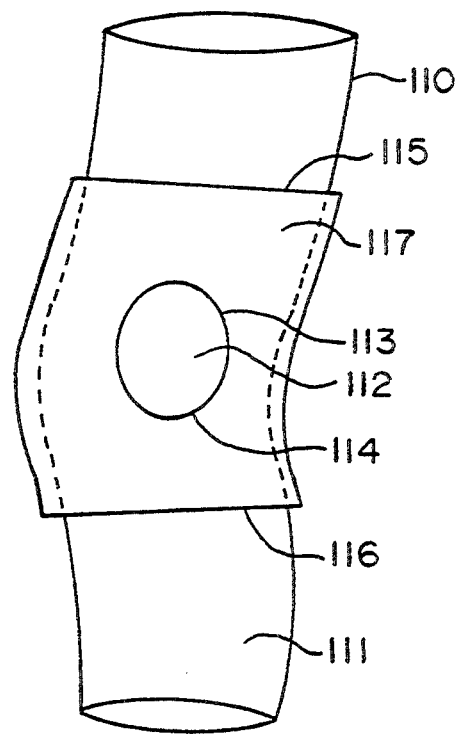
Figure 23:
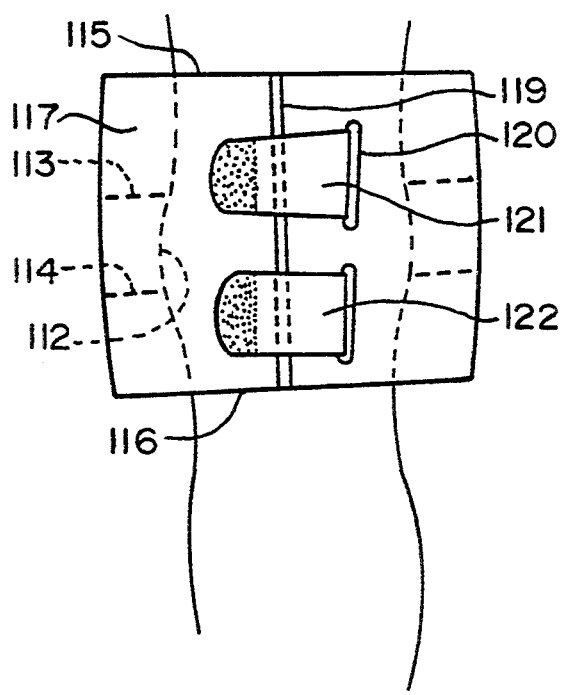

FIGS. 21-23 show a support unit around the knee. This unit is made from a unit similar to one shown in FIG. 1, and this unit has openings in each side in front of the prominent points of the knee. The lower thigh is shown by 110 and the upper leg by 111. The body of the unit is shown by 117. The upper rim of this unit is shown by 115, the lower rim by 116, prominent side of the knee by 112, the upper wall of the opening in front of this prominence by 113 and the lower wall of this opening by 114. FIG. 23 shows how the ends of this unit come together and are connected. In this view, the edge of one end is shown by 119, and a strap 121 from the other side comes to go through a snap 120 and make a U-turn and to stick to the back of the unit from which the strap came. A lower strap is shown by 122.

The unit for the knee is basically similar to the unit mentioned for the ankle, except it has a shape to match and to go around and be held on the knee joint. Its ends come and join together by snaps or a piece of Velcro ™. The shape of this unit will have a design to allow the knee to bend due to its special construction with having separate pieces in its front. So, this unit is made from combinations of two (at times more) pieces of balloon units in front; one upper piece and one lower piece. Importantly, these pieces may be connected to each other by a layer of latex. This layer of latex may be stuck or glued to the rear surface of the balloon units. This will give a great advantage of keeping their relation and shape under control and bringing them to the appropriate shape when the joint changes from a closed position to an open one. Alternatively, elastic pieces may be used to do the same job. The rear ends of the front pieces are connected to a common end and then connected to each other in the popliteal area. When the person bends the knee, the upper and lower pieces will separate to allow the bending of the joint to occur. And, when the knee is straightened, the latex layer will pull the upper and lower pieces to come together and stay close, as they should. This unit may have an opening in each side of the knee in front of its prominent points to prevent the very pointed or prominent point of its sides from touching the surface of the mattress or the inside prominence of the opposing knee. Therefore, the prominent point of the knee will be held in the air and away from the pressure. This will also give the best chance for skin care as mentioned earlier.

Figure 24:
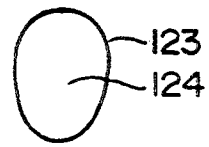
FIGS. 24 and 25 are top and side views of a part that is used with a preceding embodiment.
Figure 25:
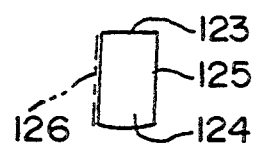

FIG. 24 shows front view of a piece of balloon that can be inserted inside opening 118 of this unit to provide a method of application of medications and support on an ulcer. Here the border of this unit is shown by 123 and its body by 124. FIG. 25 shows the side view of a piece of balloon shown in FIG. 24. The upper rim of this unit is shown by 123, body by 124, the outer surface by 125, and the soft gauze on it by 126.

Figure 26:
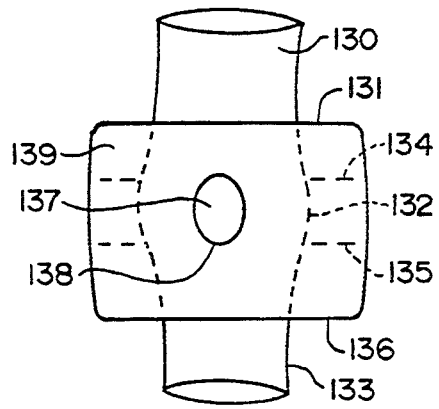
FIGS. 26 and 27 are front and right side views of a tenth embodiment in use.
Figure 27:
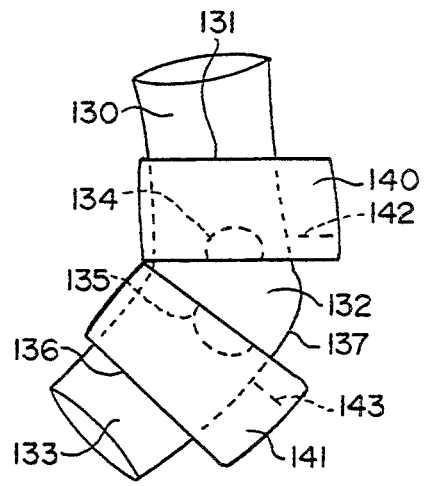

FIG. 26 shows a support unit around an elbow of a patient. This unit is made from a unit similar to one shown in FIG. 1 and has openings in each side in front of the prominent points of the elbow, as well as in front of the tip of the elbow. The lower arm is shown by 130 and the upper forearm by 133. The body of the unit is shown by 139, the upper rim by 131, the lower rim by 136, the prominent side of the elbow by 132, the rim of upper wall of the opening in front of this prominence by 134, the lower wall of this opening by 135, the tip of the elbow by 137, and the wall of the opening around the tip by 138. FIG. 27 is to show how using two pieces will allow the person to bend his or her elbow and this unit allows this to happen. In this figure, the elbow is bent. The body of the upper unit is shown by 140. The upper wall of the opening around the tip of the elbow is 142 and the lower wall of this opening is 143.

The unit for the elbow also is very similar to the units mentioned earlier for the ankle and the knees. Similar to the knee unit the shape of this unit will be made to allow the elbow to bend easily due to the separation in the posterior part of the elbow unit in front of the tip of the elbow. Also, this unit may have the openings in each side of the prominent sides of the elbow joint. Again, this construction is to prevent the direct pressure on those important prominent spots, and to allow therapeutic modalities to be given to the sore spot through the openings.

Figure 28:
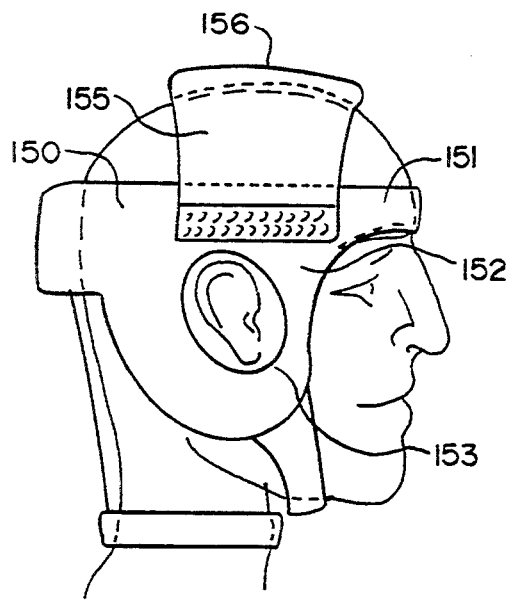
FIGS. 28 and 29 are right side and front views of an eleventh embodiment in use.
Figure 29:
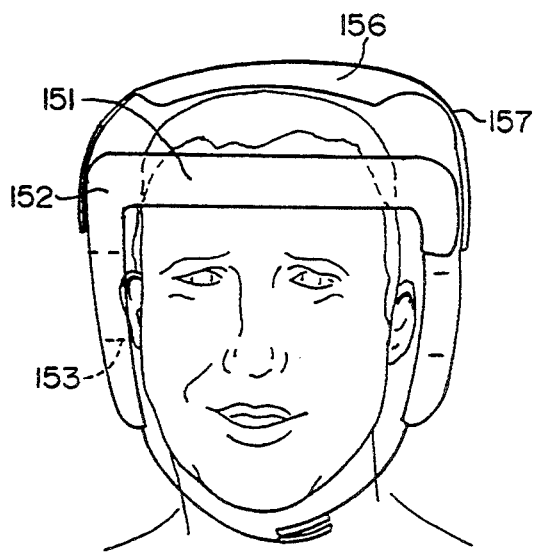

FIGS. 28 and 29 show a patient using a unit made for the head. This unit has a construction similar to the other units, except its shape is different to protect the desired places in the head. This figure shows a unit that goes around the front and the occipital area of the head and also provides protection to the ears. It is held in place by a strap going under the chin and another one connected to the back of the unit that also connects to the piece around the neck or the strap that goes to the lower chin. This unit does also allow a unit that stands against the top of the head to be held in place by its ends connecting to the sides of the unit. A front piece is shown by 151, the body of the balloon by 150, the border of the opening around the ear by 153, the strap that is in the back by 155, the top piece by 156 and its right and left sides by 155, 157. The portion in front of the ear is shown by 152. The sides of this unit are connected to each other under the chin to hold the unit in place.

The Unit for the Head

The dressing of cuts and ulcerated areas of the scalp has been a longstanding problem due to the hair in the scalp, as well as the anatomy of the area. However, this job can be very much simplified with use of a unit that has the same basic construction similar to the previous units. Naturally, this unit has a shape to go around the head and the front area. This is held in place by straps that go under the chin and in the back. This unit allows protection of different parts of the face, ears and the head, and its opening protects the areas and spots intended. It can have an opening to protect the back of the head from pressure too. A particular unit that has an opening in the top allows the bandaging and support of the operated areas of the top of the head to be provided easily after certain skull or brain operations. Like the other units, these openings allow selective dressing of the area protected by openings. The other therapeutic modalities similar to the one mentioned earlier can also be provided through the openings without a need to dismantle the whole unit. The balloon patch that is used is a piece of balloon that matches the size of the opening and it may have a soft cover that will go over the dressing of the scalp and then be held in place by straps that go and stick to the sides of the unit. This is a unique way of dressing the scalp of patients, and it will make it possible to have the dressings changed easily. Importantly, a layer of thin latex with a shape to go over the scalp like a stocking with holes around the eyes and nose and face may be used to hold the pieces of this unit together and on the head and in desired way which will pull and hold the pieces in place properly. This piece will be of great help since it does not have much volume and will not take space. It will be very adaptive to the shape of the area and easily will assume the shape of the area. And, it will prevent change in the shape of the unit. This may prove to save significant time in dressings of lesions of the head.

Figure 30:
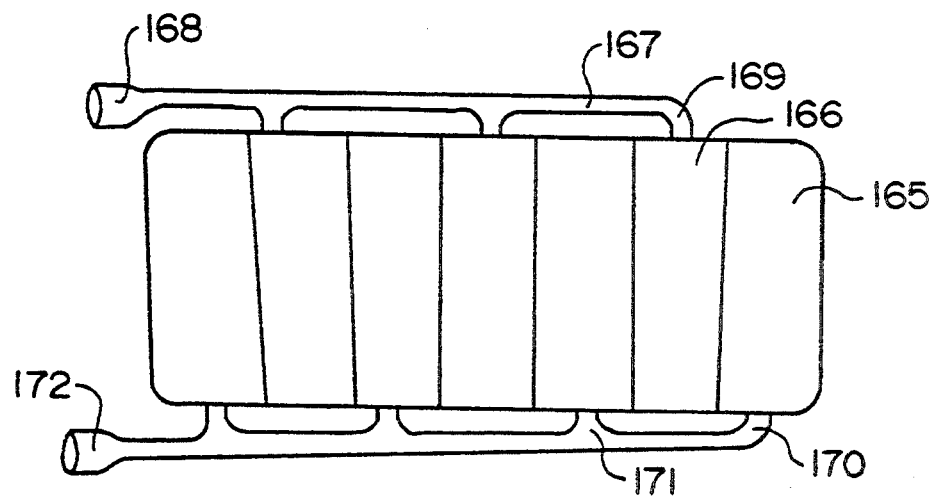
FIG. 30 is a front view of a twelfth embodiment.

FIG. 30 shows a series of balloons that are next to each other and are made by dividing one larger balloon by walls to make the smaller balloons. This unit has tubing in its upper and lower sides that works as inflation means for the alternate balloons so that each other balloon can be selectively inflated and also this will make it possible to have alternative and periodic inflation of these balloons two adjacent balloons are shown by 165 and 166, each of which is connected to a different tube. The balloon 165 is connected by opening 170 to tube 171 and finally to inflation port 172. The balloon 166 is connected by opening 169 to tube 167 and then to inflation port 168.

Figure 31:
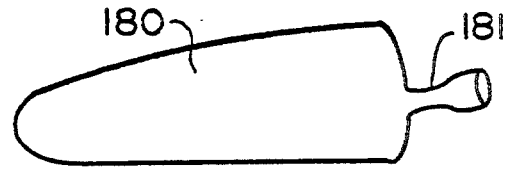
FIG. 31 is a top view of a balloon by itself.

FIG. 31 shows a front view of a balloon which has an almost triangular shape. It has its own inflation port 181.

Figure 32:
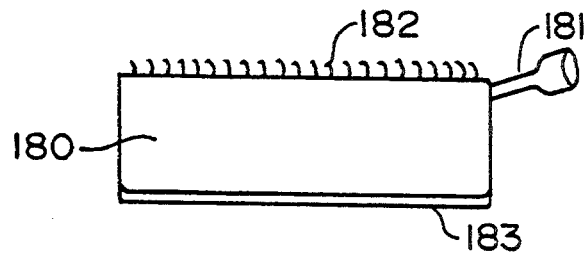
FIG. 32 is a front view of FIG. 31.

FIG. 32 shows the side view of the balloon shown in previous figure with the rear surface of this balloon covered by a rough Velcro ™ patch 182 and the front face covered by a soft cover 183. The body of the balloon is shown by 180.

Figure 33:
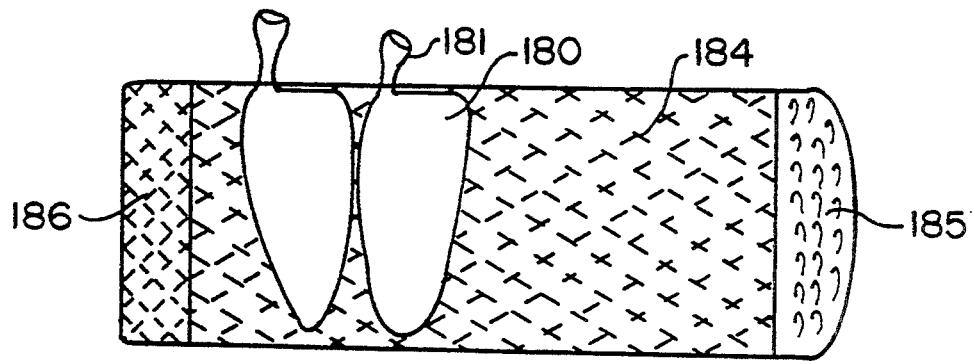
FIG. 33 is a front view of a thirteenth embodiment containing balloons like those of FIGS. 31 and 32.

FIG. 33 shows a support unit with a surface covered by Velcro ™ shown by 184. At the left side of this unit, two balloons similar to the one of FIG. 31 and 32 are stuck. The ends of this unit are shown by 185 and 186.

Figure 34:
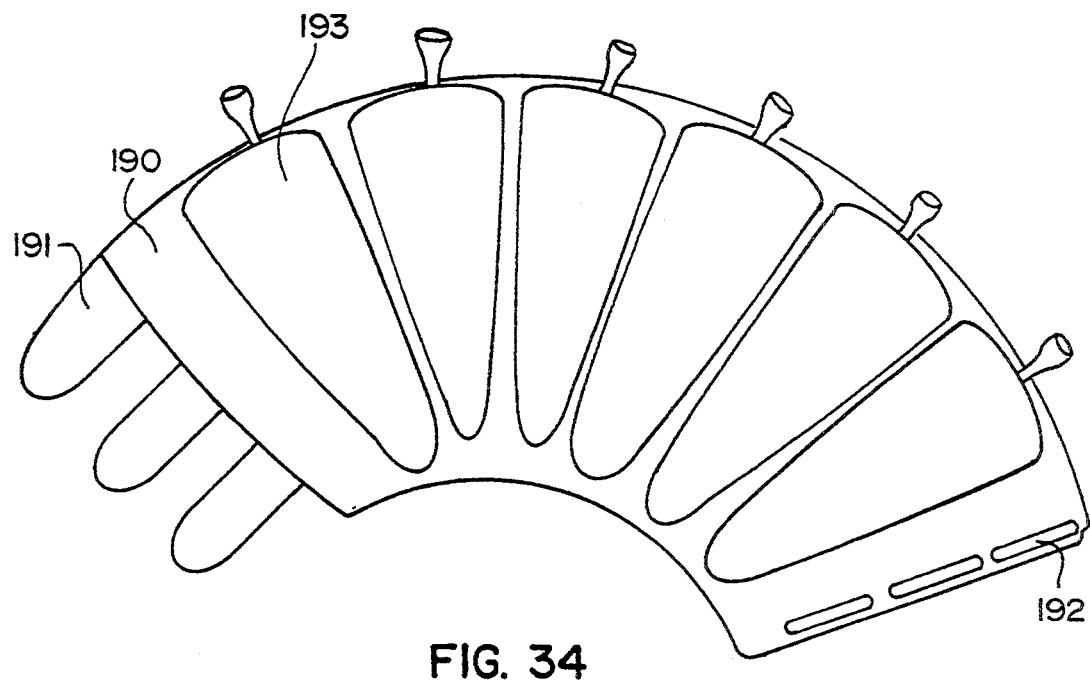
FIG. 34 is a front view of a fourteenth embodiment containing balloons like those of FIGS. 31 and 32.

FIG. 34 shows a support unit similar to the one shown in the previous figure, except this unit has a shape which is rounded and is covered by units of balloons similar to the one shown in FIG. 31. In FIG. 34, the body of the support unit is shown by 190 and a balloon by 193. One end of this support unit has straps 191, and the other end has openings 192 that will allow the straps to go through them.

Figure 35:
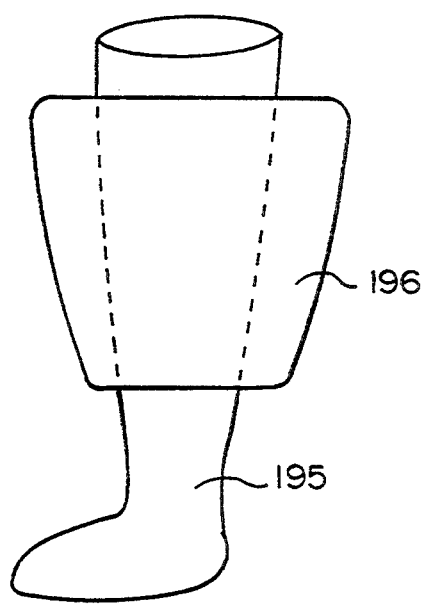
FIG. 35 shows the embodiment of FIG. 34 in use.

FIG. 35 shows a patient having a support similar to the one shown in the previous Fig. wrapped around his leg. In this view, the wrap 196 is around leg 195.

Figure 36:
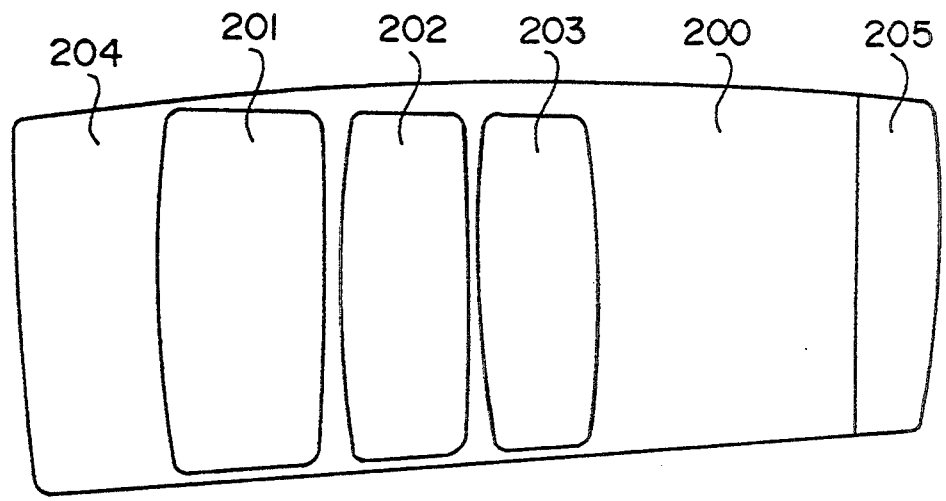
FIG. 36 is a front view of a fifteenth embodiment containing balloons.

FIG. 36 shows a support unit similar to the one shown in FIG. 33 which is covered by three balloons 201, 202, 203 that have different sizes and thicknesses. In this view, the body of the support is shown by 200, its one end by 205, and another end by 204.

Figure 37:
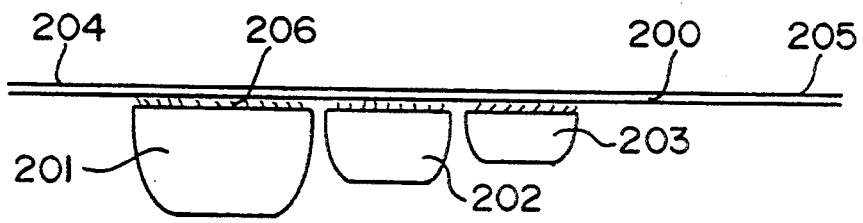
FIG. 37 is a top view of FIG. 36.

FIG. 37 shows the side view of the support unit shown in FIG. 36. This view is to shown how the thicknesses of these balloons may be different. The balloon 201 has more than twice volume of the balloon 203. This view also shows the base of these units connected to the support unit by a Velcro ™ system 206.

Figure 38:
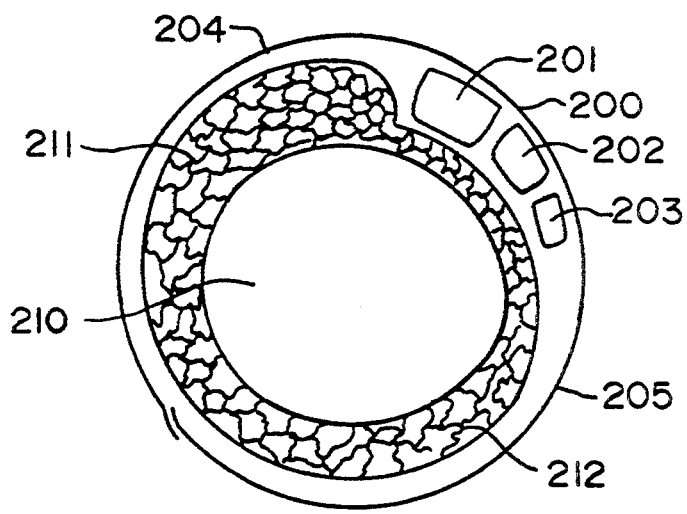
FIG. 38 is a cross section through a usage of the fifteenth embodiment.

FIG. 38 shows a supposedly obese patient who is operated with significant amount of fat removed from her one side of abdomen in the right side of the picture. Then, a combination of balloons similar to those shown in the previous Fig. is applied to prevent leakage of blood and fluid, disfigurement of the area, and to help in displacement and shaping of the area. In this view, the balloons are wrapped around the body and the abdomen. This is a cross-cut view and shows the inside of the abdomen in the center at 210 surrounded by the fat layer 211 which has some part of that removed in the right side of the picture and replaced by the balloons. The support 200 is shown with its ends 204, 205 extending to the sides to wrap around the body. The balloons 201, 202, 203 almost match and compensate for the amount of fat removed.

FIGS. 39–42 show a latex unit that here is chosen to show a prototype of this unit. In this case, it is a unit that will go over and around the elbow joint to hold the unit in place and also to allow the washing of the areas above and below this area to occur. This unit has a shape to go over the protective unit of the elbow and to stay in place due to its internal elastic function. In the upper as well as the lower openings of this unit, which is made to stand like a sleeve in place, there will be a couple of lines of fortified latex which are intentionally made to go all around the limb and prevent water from coming inside the unit. (This fortified area will be like adding a rubber band to the unit, and, in some cases, a rubber band may also be used for such purpose.) This will give the opportunity for a patient's body and arm to be washed and cleaned without contaminating the area. Small tabs of elastic are placed outside of the ends of this unit to make it possible for the elastic ends to be held and pulled. The upper end of this unit is 220, the one of the fortified lines in the upper area is 225, the body of the unit is 221, and expandable area to stand in front of the tip of elbow is 224. The lower end is 223 and one line of fortified latex is 226. The tabs of the upper end are 230, 231 and 232, and in the lower end they are 233, 234 and 235.

FIG. 40 shows the special design of the area which is to stand at the tip of elbow. This area is shown by 224 and is designed to have extra latex which will make a wall like that of an accordion. This will allow the unit to expand in this side when the elbow is bent. I believe this is a great advantage that will prevent change of shape and function of the unit in this area when the elbow is bent. This will also be true in units made for knee or hip, etc. to give a better functional unit.

FIG. 41 shows a patient using the unit on his elbow. This figure shows how the upper and lower ends of this unit function like a sleeve and are reasonably tight around the place. This figures show that the bend of the elbow has not caused much of a problem in the tip of the elbow.

FIG. 42 shows the opening of the upper part of this unit and the positions of the small tabs. In this Fig., 220 is the inside of the opening and 229 is the wall of the opening. The small tabs look in this view like a line and they are marked in each side by 232, 231, 230 and 236.

A Unit for the Wrist (not shown) is basically similar to the previous units for the support of the other joints except the shape of the unit will match the shape of the wrist and upper hand. The unit is made from one piece for immobilization of the wrist, and a unit made from multiple pieces will allow motion of the wrist to occur. The unit can be wrapped and be closed from the front or the back, whichever appears more appropriate for the case.

In order to prevent skin problems and infections and to give better care and cleanness to an area, a disposable lining made from soft absorbing material, such as cotton, that will have a shape to match and go around the joints mentioned above will stay under the units and be exchanged daily for better care of the skin and the area. The ends of this lining have an adhesive rim or bands with adhesive surface covered and supported by a layer of plastic that is removed to allow the connection of the edges to occur. The size and shape of this lining will vary. In practice, this lining is used under the unit and the unit is applied on it. In these cases, the inner surfaces of the unit do not need to have a very fine lining since the liners will do their job. However still the inner surface of the unit has to be soft and comfortable.

The idea of using balloons for support is very unique and useful and can be used in other cases too. I believe it will be very helpful in many other circumstances. This will be specially true after surgeries for prevention of bleeding and holding the operation site stable. I would like to say though that it is not always possible for a complete unit to be made for every case. To solve this problem and to have more choices which always is better, a support unit can be made from a soft, non-stretchable fabric that has a surface covered with patches of Velcro TM. This unit will allow sticking different size and shapes of balloons that have a rear surface with a matching patches of Velcro TM so that these combinations will allow particular and more appropriate balloons to be chosen and be applied in place with use of the support system. This will also give the chance of changing the balloons when it comes to be necessary and also when a balloon is popped or torn.

These balloons may have their own inflation ports to allow them to be inflated individually to the level desired or to be connected to a connection tube that will allow groups of the balloons to be inflated by one port. This unique construction will give the chance to choose different size balloons and to make a customized unit for a particular patient to match his or her size and condition and special location, the need for use exists. The shapes of the balloons can be different and vary significantly.

The need for such units may be easy to understand when we consider that the size of people and the types of surgery they undergo is different, and that a need for many options is real for choosing a unit to be used in special circumstances. For example, I want to be open and give my own reason for stressing this matter. In my free imaginations, one time I thought to find a way to help a nice nurse that I see occasionally in my job. She is not my patient and has not complained to me about her problem. However this has not prevented me from thinking about a solution for that young lady and the people like her that in my observation do suffer tremendously from the very heavy weight they have. I have no question in my mind that their morbid weight will cause them a major complication if not corrected. This has been true about some of my other patients, and I have reached a conclusion in my own mind that we should be able to operate on these patients to remove fat or to do lipo-suction periodically to remove the tremendous extra fat and related heavy weight to diminish the job of their heart and lungs and joints, etc. The fact that my patients, even after referral to major centers have not received help, make me believe that there is no help available. This makes me think about removing those fat masses surgically with a strong medical back up. In finding a solution I thought that after a mass of fat is removed, it would be much better, if not necessary, to apply a pressurized balloon in the area to prevent bleeding from the area, fluid accumulation in the area, and looseness of the skin, etc.

The balloons will help to maintain a symmetrical shape for the patient until the total plan of treatment is carried out. Also, more importantly, the pressure from the unit and the balloons may help in reshaping the rest of the fat in the operation area under the skin to prevent lumps of fat from being accumulated and to stay in one point when more likely the pressure will help in reshaping the surface under it to be smoother and better. To illustrate my reason behind the need for many and multiple shape balloons, I would like to use this example that in such case a surgeon may have to remove the fat only from one side of the abdomen to prevent very extensive intervention and to leave the other side for the next time, and also to work in another side such as the thigh or leg or arm, etc. Also, let us consider a case after surgery for varicose veins which I believe a long balloon to apply pressure to the procedure site will be very beneficial, and this is also a case to show a need for different units. And for this reason, I decided to introduce these particular units that will give the chance of making a variety of different balloons. And I want also to choose this example to claim that these units will also be very useful after many surgeries for prevention of hematoma and bleeding, etc., after the surgery.

So there is need for variety of balloons that some may be inflated as group and, in some cases, we may wish to inflate them periodically to avoid a constant pressure to one area to compromise circulation, etc. In some cases, the time may dictate us to change the size of the balloon, etc. However I have no doubt in my mind that these units will be very effective.

I also believe that these units may be used effectively to press a focal site such as side of the thigh or legs or buttocks of people, mostly ladies, to help them to lose fat in that particular spot which is a very, very important cosmetic problem for some women and unfortunately brings it's psychological reaction and problem with their self-image and does cause marital problems.

I believe the units I introduced will prove over the time to show their great advantages and to help many patients. That is the reason I am proceeding with this application.

What is claimed is:

1. A support device comprising balloon means comprising a facing for confronting a portion of the body, a soft layer covering said facing so as to lie between said balloon means and said body portion, and strapping extending from opposite ends of said balloon means and forming in cooperation with said balloon means, a wrapping for encircling said body portion and applying pressure of said balloon means to said body portion, and further including a further layer between said balloon means and said soft layer, said further layer comprising soft plastic bubbles sandwiched between two layers of soft plastic.

2. A support device comprising balloon means comprising a facing for confronting a portion of the body, a soft layer covering said facing so as to lie between said balloon means and said body portion, and strapping extending from opposite ends of said balloon means and forming in cooperation with said balloon means, a wrapping for encircling said body portion and applying pressure of said balloon means to said body portion, in which said balloon means comprises plural balloons, each of which is separately inflatable by its own inflation port and each of which is separably secured to said strapping by a fastening system.

3. A support device as set forth in claim 2 in which said soft layer comprises individual portions, each applied to an individual one of said plural balloons.

4. A support device as set forth in claim 3 in which said plurals balloons are each generally triangular in shape.

5. A support device as set forth in claim 2 in which said plural balloons are constructed to have different overall thicknesses in the direction of pressure application to said body portion when they are inflated.

6. The combination of a support device as set forth in claim 2 and a disposable liner said disposable liner for wrapping around said body portion in underlying relation to said support device.

7. The combination of a support device and an insert, said support device comprising balloon means comprising a facing for confronting a portion of the body, a soft layer covering said facing so as to lie between said balloon means and said body portion, and strapping extending from opposite ends of said balloon means and forming in cooperation with said balloon means, a wrapping for encircling said body portion and applying pressure of said balloon means to said body portion, in which said balloon means comprises an open area for fitting over a bony prominence or ulcerated area of said body portion so that said balloon means is disposed in surrounding relationship to said bony prominence or ulcerated area, and an insert supported on said support device and disposed within said open area for applying medicine to said bony prominence or ulcerated area free of the pressure of said balloon means.

8. A support device as set forth in claim 2 in which said plurals balloons are each generally triangular in shape.

9. The combination of a support device and insert as set forth in claim 7 in which said bony prominence or ulcerated area of said body portion is disposed proximate an end of an axis of a joint of said body and said balloon means comprises said open area and said insert being disposed relative to said balloon means so as to be located at said end of said axis about which said joint flexes when said support device and insert are applied to said body portion.

10. A support device as set forth in claim 9 in which said wrapping is constructed to allow said joint to flex about said axis.

* * * * *